United States Patent
Barsoum et al.

(10) Patent No.: US 10,595,943 B2
(45) Date of Patent: Mar. 24, 2020

(54) MODEL-BASED SURGICAL PLANNING AND IMPLANT PLACEMENT

(71) Applicant: THE CLEVELAND CLINIC FOUNDATION, Cleveland, OH (US)

(72) Inventors: Wael K. Barsoum, Bay Village, OH (US); Juan Suarez, Cleveland, OH (US); Preetesh Patel, Cleveland, OH (US); Kyle Walker, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/836,117

(22) Filed: Dec. 8, 2017

(65) Prior Publication Data

US 2018/0161101 A1 Jun. 14, 2018

Related U.S. Application Data

(60) Provisional application No. 62/431,559, filed on Dec. 8, 2016.

(51) Int. Cl.
*A61B 34/10* (2016.01)
*A61B 5/00* (2006.01)
(Continued)

(52) U.S. Cl.
CPC ............. *A61B 34/10* (2016.02); *A61B 5/11* (2013.01); *A61B 5/4504* (2013.01);
(Continued)

(58) Field of Classification Search
CPC .................................................. A61B 34/10
See application file for complete search history.

(56) References Cited

U.S. PATENT DOCUMENTS

| 6,917,827 B2 | 7/2005 | Kienzle, III |
| 7,660,623 B2 | 2/2010 | Hunter et al. |

(Continued)

FOREIGN PATENT DOCUMENTS

| KR | 20090093117 A | 9/2009 |
| WO | 2006/129087 A1 | 12/2006 |

(Continued)

OTHER PUBLICATIONS

Widmer, K-H., and B. Zurfluh. "Compliant positioning of total hip components for optimal range of motion." Journal of Orthopaedic Research 22.4 (2004): 815-821.

(Continued)

*Primary Examiner* — Daniel L Cerioni
*Assistant Examiner* — Yasmeen S Warsi
(74) *Attorney, Agent, or Firm* — Tarolli, Sundheim, Covell & Tummino LLP

(57) ABSTRACT

Systems and methods are provided for model-based surgical planning. A surgical planning system can include a pre-screening tool configured to provide an initial classification of a set of patients according to a pelvic tilt, measured as a position of a pelvis of the patient relative to the position of a spine of the patient, in a plurality of body positions. A model constructor is configured to construct a model of a pelvis of the patient according to the initial classification of the patient. A finite element modeling component is configured to simulate relative motion of the model of the pelvis and a model of an implant. A patient classifier is configured to select at least one of a position of the implant and an orientation of the implant for the patient according to the simulated relative motion.

10 Claims, 3 Drawing Sheets

(51) Int. Cl.
  *A61B 34/00* (2016.01)
  *A61F 2/46* (2006.01)
  *A61F 2/32* (2006.01)
  *A61B 5/11* (2006.01)
  *A61B 34/20* (2016.01)

(52) U.S. Cl.
  CPC .......... *A61B 5/4561* (2013.01); *A61B 5/4566* (2013.01); *A61B 34/25* (2016.02); *A61F 2/32* (2013.01); *A61F 2/468* (2013.01); *A61B 5/0073* (2013.01); *A61B 34/20* (2016.02); *A61B 2034/101* (2016.02); *A61B 2034/104* (2016.02)

(56) References Cited

U.S. PATENT DOCUMENTS

| | | | |
|---|---|---|---|
| 7,835,779 | B2 | 11/2010 | Anderson et al. |
| 8,057,479 | B2 | 11/2011 | Stone |
| 8,271,066 | B2 | 9/2012 | Sarin et al. |
| 8,781,556 | B2 | 7/2014 | Kienzle, III |
| 9,138,319 | B2 | 9/2015 | Fanson et al. |
| 2008/0255442 | A1 | 10/2008 | Ashby et al. |
| 2014/0052149 | A1 | 2/2014 | Van Der Walt et al. |
| 2015/0088145 | A1 | 3/2015 | McCarthy |
| 2017/0128135 | A1* | 5/2017 | McCarthy .............. A61B 34/10 |

FOREIGN PATENT DOCUMENTS

| | | |
|---|---|---|
| WO | 2012/097873 A1 | 7/2012 |
| WO | 2016/180439 A1 | 11/2016 |
| WO | 2017/027772 A1 | 2/2017 |

OTHER PUBLICATIONS

Tamura, Satoru, et al. "Hip range of motion during daily activities in patients with posterior pelvic tilt from supine to standing position." Journal of Orthopaedic Research 33.4 (2015): 542-547. APA.

Brown, Thomas D., et al. "Impingement and dislocation in total hip arthroplasty: mechanisms and consequences." The Iowa orthopaedic journal 34 (2014): 1.

Nadzadi, Mark E., et al. "Kinematics, kinetics, and finite element analysis of commonplace maneuvers at risk for total hip dislocation." Journal of biomechanics 36.4 (2003): 577-591.

Shariff, Raheel, et al. "Kinematic assessment of hip movement when retrieving an object from the floor." Journal of orthopaedic surgery and research 6.1 (2011): 11.

Charbonnier, Caecilia, et al. "Analysis of hip range of motion in everyday life: a pilot study." Hip International 25.1 (2015): 82-90.

Charbonnier, Caecilia, et al. "Sexual activity after total hip arthroplasty: a motion capture study." The Journal of arthroplasty 29.3 (2014): 640-647. APA.

PCT International Search Report and Written Opinion for corresponding Application Serial No. PCT/US2017/065338, dated Jun. 13, 2018, pp. 1-18.

* cited by examiner

MODEL-BASED SURGICAL PLANNING AND IMPLANT PLACEMENT

RELATED APPLICATIONS

This application claims priority from U.S. Patent Application Ser. No. 62/431,559, filed 8 Dec. 2016, which is incorporated herein in its entirety.

TECHNICAL FIELD

This invention relates to surgical planning, and more particularly, to model-based surgical planning and implant placement.

BACKGROUND OF THE INVENTION

A surgical procedure that restores the integrity and function of a joint is generally referred to as arthroplasty. The surgical replacement of joints or joint surfaces with prosthetic implants due to injury or degeneration has become the most common arthroplasty procedure. In fact, hip replacement, including total hip arthroplasty and hemiarthroplasty, is currently the most common orthopedic operation. While the purpose of hip replacement is to increase the patient's quality of life by improving muscle strength, relieving pain, restoring range of motion, and improving walking ability, both short-term and long-term patient satisfaction with hip replacement varies widely.

SUMMARY

The present disclosure relates generally to surgical planning for implant placement and, more specifically, to devices, systems, and methods for surgical planning. In some examples, surgical planning in accordance with an aspect of the present invention can increase both short-term and long-term patient satisfaction with arthroplasty procedures, such as hip replacement.

In one aspect, a surgical planning system can include at least one non-transitory computer readable medium storing computer executable instructions and at least one processor to execute the computer executable instructions. The instructions include a prescreening tool configured to provide an initial classification of a set of patients according to a safe zone determined from a pelvic tilt, measured as a position of a pelvis of the patient relative to the position of a spine of the patient, in a plurality of body positions. A model constructor is configured to construct a model of a pelvis of the patient according to the initial classification of the patient. A finite element modeling component is configured to simulate relative motion of the model of the pelvis and a model of an implant. A patient classifier is configured to select at least one of a position of the implant and an orientation of the implant for the patient according to the simulated relative motion.

In another aspect, a method for surgical planning includes providing an initial classification of a patient according to a safe zone determined from a pelvic tilt of the patient in a plurality of body positions. The pelvic tilt is measured as a position of a pelvis of the patient relative to the position of a spine of the patient. A model of a pelvis of the patient is constructed according to the initial classification of the patient, and relative motion of the model of the pelvis and a model of an implant is simulated. At least one of a position of the implant and an orientation of the implant is selected for the patient according to the simulated relative motion.

In another aspect, a method for surgical planning includes affixing a set of sensors to the patient and instructing the patient to assume a plurality of body positions, The change of orientation of the sensors is recorded as the patient moves through the plurality of body positions to measure a change in a pelvic tilt of the patient. A size of a safe zone of the patient is estimated from the measured change in pelvic tilt across the plurality of body positions.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1:
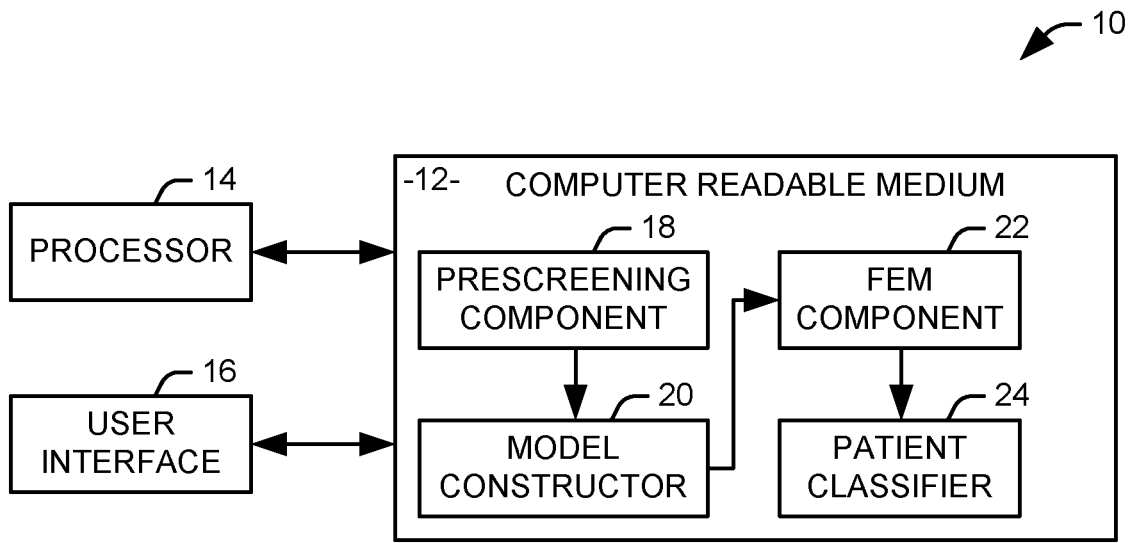
FIG. 1 illustrates a system that can employ model-based surgical planning.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "arthroplasty" can refer to the surgical reconstruction or replacement of a joint (e.g., hip, knee, elbow, shoulder, ankle, finger, etc.). In some examples, arthroplasty can include total or partial joint replacement surgery. In other examples, arthroplasty can include a joint resurfacing procedure.

As used herein, the term "surgical planning" can refer to a preoperative method that allows features of a surgical procedure to be pre-defined. For example, one type of surgical planning can involve the selection, location, and/or orientation of an implant to replace at least a portion of a joint in a total or partial joint replacement surgery as well as the selection of a surgical approach for placing the implant.

As used herein, the term "model" can refer to a representation of an object created on a computer. In some instances, the model can be a three-dimensional representation of the object, either as data stored on a non-transitory computer readable medium or media or a physical object, for example, produced via a rapid prototyping process.

As used herein, the term "standing position" can refer to a position in which the patient is in an upright position supported by his or her feet. The term "sitting position" can refer to a position in which the patient's torso is substantially upright while body weight is supported primarily by the buttocks in contact with the ground or a horizontal object such as a chair seat. The term "supine position" refers to a position in which the patient is lying horizontally with the face and the torso facing upwards. Each of these positions represents a position of the pelvis relative to the spine, although it will be appreciated that these three positions are not an exhaustive list of such positions.

As used herein, an image is a two-dimensional or three-dimensional representation of either or both of a portion of a patient's anatomy and an implant obtained via capture and evaluation of electromagnetic radiation and. An image can be digital or analog. These images can be acquired with a number of different imaging modalities, including: radiography, computed tomography, and magnetic resonance imaging.

The term "coordinate system" can refer to a system of representing points in a space of given dimensions by coordinates.

As used herein, the terms "subject" and "patient" can refer, interchangeably, to any warm-blooded organism including, but not limited to, a human being, a pig, a rat, a mouse, a dog, a cat, a goat, a sheep, a horse, a monkey, an ape, a rabbit, a cow, etc.

One aspect of the present disclosure, as shown in FIG. 1, includes a system 10 that can employ surgical planning for hip arthroplasty. It will be appreciated, however, that the system 10 could be used for other implant procedures for which a suitable anatomic orientation, such as the pelvic tilt, discussed below, can be derived from an anatomically defined plane based on bony, reproducible landmarks. In the shoulder, for instance, a "scapular plane" can be defined, and the orientation of the implant and any safe zones for implantation, can be defined from this plane. The safe zone has historically been defined by the acetabular cup orientation with respect to the anterior pelvic plane, which is established on the solid body pelvis by the Anterior Superior Iliac Spines (ASIS) bilaterally and the most anterior point of the pubis, however other planes of reference can be utilized either directly with respected to the plane (i.e. the plane of the acetabular rim) or indirectly by referencing the anterior pelvic plane. This system can utilize any of these planes to report a safe zone for component orientation.

The system 10 includes a non-transitory memory 12, a processor 14, and a user interface 16. In some instances, the computing device 10 can utilize the non-transitory memory 12 to store computer-executable instructions and the processor 14 to execute the computer-executable instructions to facilitate the performance of operations and/or implement the functions of one or more of components of the system. For example, the computing device 10 can be a general purpose computer, special purpose computer, and/or other programmable data processing apparatus. Accordingly, the non-transitory memory 12 can be any non-transitory medium that is not a transitory signal and can contain or store the program for use by or in connection with the instruction or execution of a system, apparatus, or device. For example, the non-transitory memory 12 can be an electronic, magnetic, optical, electromagnetic, infrared, semiconductor system, apparatus or device, a portable computer diskette, a random access memory, a read-only memory; an erasable programmable read-only memory (or Flash memory), or a portable compact disc read-only memory. It will be appreciated that the system 10 can incorporate multiple devices, with multiple processors and memories (not shown).

The non-transitory memory 12 can store components of the model-based surgical planning tool that are executable by the processor 14. The model-based surgical planning tool can be used to plan a patient-specific arthroplasty procedure, where implant selection and orientation are based on minimalizing dislocation risk and decreasing wear considerations. In the illustrated implementation, components of the surgical planning tool can include a prescreening component 18, a model constructor 20, a finite element modeling (FEM) component 22, and a patient classifier 24.

The surgical planning tool focuses on identifying a set of positions and orientations, specifically values for inclination and version for an acetabular cup of the implant having a low risk of dislocation and good wear characteristics, referred to herein as a safe zone. For the purposes of determining the safe zone, the risk of dislocation can be considered to vary inversely with impingement-free range of motion of the joint, and good wear characteristic include low amounts of edge loading on the implant and/or a better distribution of force across the implant surface area. It should be noted here that the inventors have found that the safe zone for a given patient does not necessarily correspond to, or for that matter, overlap with, the Lewinnek safe zone. Due to variations in anatomy, for example, differences in pelvic tilt and positional variation in pelvic tilt, the size of safe zones will vary significantly across patients. Some patients will have larger safe zones, allowing for more freedom in the placement of the acetabular cup, while other patients will have narrow safe zones, requiring significant precision in the acetabular cup placement to achieve optimal results. In some patients, no orientation of the cup will provide the desired dislocation risk and wear characteristics, and the safe zone will consist of a region associated with a best combination of these factors.

In the implementation discussed in detail herein, the safe zone for patient is two-dimensional, based on determining a safe orientation for an acetabular cup in a hip arthroplasty procedure. It will be appreciated, however, that the safe zone can have more than two dimensions, for example, based on a position of the acetabular cup. In one implementation, safe zone for patient is three-dimensional, based on the depth, version, and inclination of acetabular cup. Further, the method can be applied to a femoral implant, to determine a safe zone for the position and orientation of the femoral implant. For example, one implementation can utilize a three-dimensional safe zone for the femoral component of the implant, based on the version, offset, and height of the femoral component. In another implementation, the determination of the safe zone for implant placement can include parameters representing each of the acetabular cup, the femoral implant, and alterations to the implant site, such as reaming.

The prescreening tool 18 is configured to provide an initial classification of a set of patients according to an expected size of their safe zone. In one implementation, a pelvic tilt of the patient is measured in at least one position of the pelvis with respect to the long axis of the spine and/or relative to the relative to the gravitational plane, and the patient is classified according to the measured pelvic tilt. The various positions can include any positions associated with dislocations or impingements, including standing straight, sitting, standing with hips bent at ninety degrees, or supine. In another implementation, a change in the pelvic tilt between positions can be measured, either directly or by measuring the pelvic tilt at multiple positions, and the patient is classified according to the according to the size of their safe zone. In one implementation, a set of sensors, for example, accelerometers, can be affixed to the patient, and the change of orientation of the sensors can be measured as the patient moves through positions. In one example, a smart phone or similar device can be used, with the control software for taking the measurements stored as an application on the device.

The inventors have determined that the size of a patient's safe zone can be determined via a change in pelvic tilt between positions. Accordingly, in one implementation, a linear combination of the pelvic tilt at a plurality of positions is utilized as a classification metric according to a set of user selected weights. In another implementation, the prescreening tool 18 can be loaded with a plurality of representative heat maps. A given heat map provides a two-dimensional mapping for each implant can be determined, representing a desirability of each coordinate set as a desirability score calculated according to a likelihood of impingement or dislocation. The desirability score can be determined as a numerical or categorical value. Each representative heat map can represent average values (e.g., mean, median, or mode) over a number of number of heat maps taken for patients with a similar pelvic tilt. A composite heat map can be taken by combining these representative heat maps over multiple body positions with measured pelvic tilts to determine a projected overall safe zone. For example, all desirability scores that do not meet a threshold value in all representative safe zones can be excluded from the overall safe zone. Alternatively, the values can be averaged across the body positions. The patient's initial classification can be determined from the size of this projected safe zone.

The model constructor 20 constructs a model of the patient's pelvis to facilitate an evaluation of the implant placement. To limit unnecessary exposure of the patient to ionizing radiation, the model construction process can be responsive to the determination at the prescreening component 18, such that the model for different patients can be constructed differently depending on the initial class to which the patient was assigned. For example, where the patient is determined to have a large safe zone, a default pelvic model can be adapted for that patient according to a measured pelvic tilt at each position and external physical measurements of the patient, as opposed to determining these values via imaging. Where the patient is determined to have a small safe zone, a full computed tomography (CT) scan of the patient's pelvis can be acquired and provided to the system for use in constructing the model.

In one implementation, patients determined to have a medium-sized safe zone can utilize imaging means with less radiative exposure than a CT scan. In this implementation, the surgical planning tool can receive a plurality of two-dimensional standing images of the pelvis. In one example, the images comprise two radiographic (or x-ray) images of the pelvis taken as substantially orthogonal views. The model can then be constructed from the captured images by warping an atlas model of the pelvis to register it to the captured images. In another implementation, a single radiographic image can be captured and used to construct the model. The position of the pelvis at one or more other positions can be determined from the standing image or images of the patient. These models can be used even for patients expected to have a small safe zone, with the CT scan deferred until the small safe zone is confirmed. It will be appreciated that in practice, the specific method for constructing the model, based on the output of the prescreening component 18, can be a recommendation to the surgeon, who would make a final decision on the imaging used in generating the model.

A potential implant is then selected and evaluated at the finite element modeling component 22. A virtual model of the implant is instantiated inside a finite element model of the joint in an initial orientation. In some instances, the model of the implant (e.g., with characteristics including size, shape, material, etc.) can be selected based on the initial pelvic model, as well as one or more biometric parameters of the patient. The model of the implant can include an acetabular cup component and a femoral ball component.

The finite element modeling component 22 works in concert with the patient classifier 24 to evaluate a safe zone of the patient and recommend one or more of a position and orientation for the implant and identify locations for which impingement is likely. Specifically, the finite element model of the pelvis and the implant can simulate various patient motions, with the risk of excessive wear and dislocation evaluated for each of a series of motions according to component interrelation and the relation of components to neighboring bones and tissue structures. The series of motions can be selected as both common motions and motions that the inventors have identified as likely to cause dislocations, such as lining up a putt, swimming, and activities of daily living. The series of motions can include osseous and component range of motion simulations can be run to measure the arc of motion possible without impingement for the different components. The osseous simulations can measure the angle to impingement between the femur and the osseous pelvis. The component simulations can measure the angle to impingement between the components with varied acetabular orientations. The combined result can take the smaller angle to impingement for each motion to represent the arc of motion possible without impingement.

In accordance with an aspect of the present invention, the series of motions can be repeated for each of a number of orientations of the acetabular cup. Each orientation can be defined by two coordinates, an inclination and a version, and a two-dimensional mapping for each implant can be determined, representing a desirability of each coordinate set as a desirability score. Accordingly, a safe zone specific to a given implant for a given patient can be determined as a region of scores for which the desirability score is above a threshold value. It will be appreciated that, while this metric is described herein as a desirability score for which high values are desirable, it could easily be designed as a risk score for which low values are desirable.

The desirability score for each patient can include an edge loading score and an impingement score, determined from the simulated motions in the finite element model. The edge loading score can be based on the contact area between various aspects of the implant under various conditions. The impingement score can be based on implant-on-implant impingement, implant-on-bone impingement, and/or bone-on-bone impingement. It will be appreciated that, in some applications, the distribution of desirability scores is substantially unimodal over the coordinates of interest, and thus the system 10 may not test every possible set of inclination and version. The desirability score can represent a weighted combination, for example, a linear combination, of these two values. The weights for this combination can be predefined values set by a user or values that are dynamically defined according to an artificial intelligence scheme. Further, the desirability score can have threshold maximum values, such that an edge loading score or impingement score above a maximum value can result in a minimum desirability score. Once all of the scores have been classified, a two-dimensional mapping of the desirability scores can be provided.

The two-dimensional mappings for each motion of the series of motions can be combined to provide a final mapping. This can be done, for example, as an average of the desirability scores across the plurality of motions, altered such that any inclination and version pair having a minimum desirability score or a score below a threshold value for any motion is given the minimum desirability score in the final map. In one implementation, the average can be a weighted average according to the likelihood that the patient would perform the motion. For example, a swimming motion might be weighted lower than a motion representing rising from a seated position for most patients. These weights can be determined to be patient specific, such that they are based on likelihood of a specific patient performing the motions, for example, based on a patient activity profile provided by the patient. Where the region of high desirability in a generated map is below a threshold area, a suggestion to select an alternate implant can be given, with an implant having a largest safe zone selected, or recommended to the surgeon, for the final procedure. As discussed in more detail below, the surgeon can also be provided with a location most likely to experience impingement for a given implant orientation, which can guide the surgical approach.

Once a final map is generated, the patient can be classified into a final class, representing the size of the safe zone for the selected implant. This classification can be used to recommend a specific surgical tool to be employed for the arthroplasty. For example, if the patient is determined to have a large safe zone, that is, a safe zone having an area above a first threshold value, a standard implantation can be recommended. If the patient is determined to have a small safe zone, that is, a safe zone having an area above a second threshold value, a precision tool can be recommended, such as a robotic implantation or the use of a patient specific implant to guide the implant placement. It will be appreciated that a CT scan of the patient can be acquired at this time to guide the implant placement. For patients having safe zone areas falling between the first and second threshold values, other factors, such as an experience of the surgeon or various biometric parameters of the patient might be factored into the recommendation.

Alternatively, a sensor based system, referred to as a "smart impactor" can be applied that allows the surgeon to identify the bony landmarks near the implant site in the operating room and then register the axis of the smart impactor against the real-world anterior pelvic plane to ensure that the cup is positioned correctly. For example, the landmarks can include the Anterior Superior Iliac Spines (ASIS) and the most anterior point of the pubis. For example, the device can be instrumented with accelerometers to determine an orientation of the device relative to gravity, and thus to the anterior pelvic plane in a real-world coordinate system. These sensors can work in concert with a sensor affixed to the patient to track motion of the pelvis during surgery to ensure a precise placement of the implant based on a target selected by the surgeon. In one implementation, the smart impactor can provide an audible or visible indication that the impactor is in the target position and orientation. In another implementation, a numerical readout can either show a variation from the target position and/or orientation or the inclination and version of the device.

It will be appreciated that, just as bony landmarks within the operative field can be used to established angular orientation of the component(s), these landmarks can be used to guide and inform the surgeon regarding translational positioning of the component(s) including anterior-posterior, superior-inferior, and medial-lateral placement. The latter of these relates directly with reaming. For instance, a virtual or physical 3-D model, created from CT or 2-D imaging can offer the surgeon visual feedback as to appropriate translational positioning and medialization (reaming). Alternatively, the smart impactor can read directly off of the landmarks around the acetabular rim to offer the surgeon information regarding depth of reaming which can be guided based on a preoperative plan.

Further, the location or locations of likely impingement, given a determined location, orientation, and implant type, can be provided to a surgeon to guide the surgical approach. For example, if dislocation was determined to be more likely to occur anteriorly, the surgeon might choose to avoid an anterior approach as that approach might increase the likelihood of dislocation due to disrupting the soft tissues in that area. When the ideal implant orientation and implant selection is achieved and locations of likely impingement have been identified, the selected implant can be surgically implanted into the patient.

Figure 2:
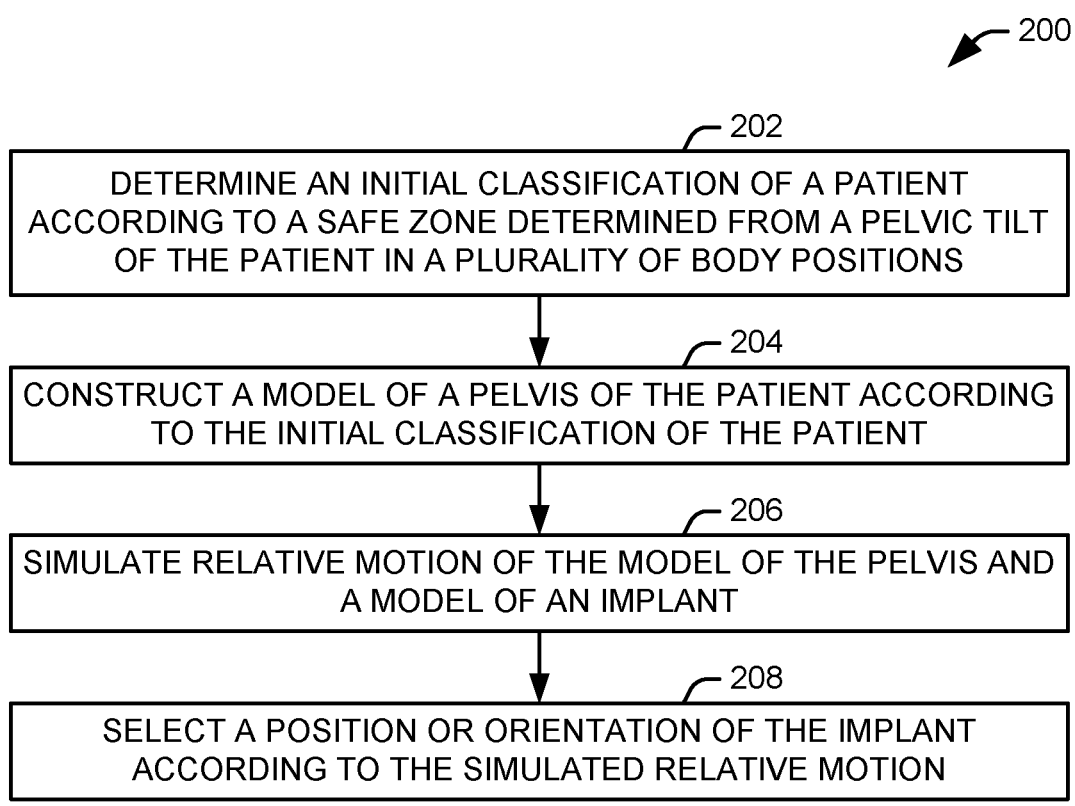
FIG. 2 illustrates a method for surgical planning.
Figure 3:
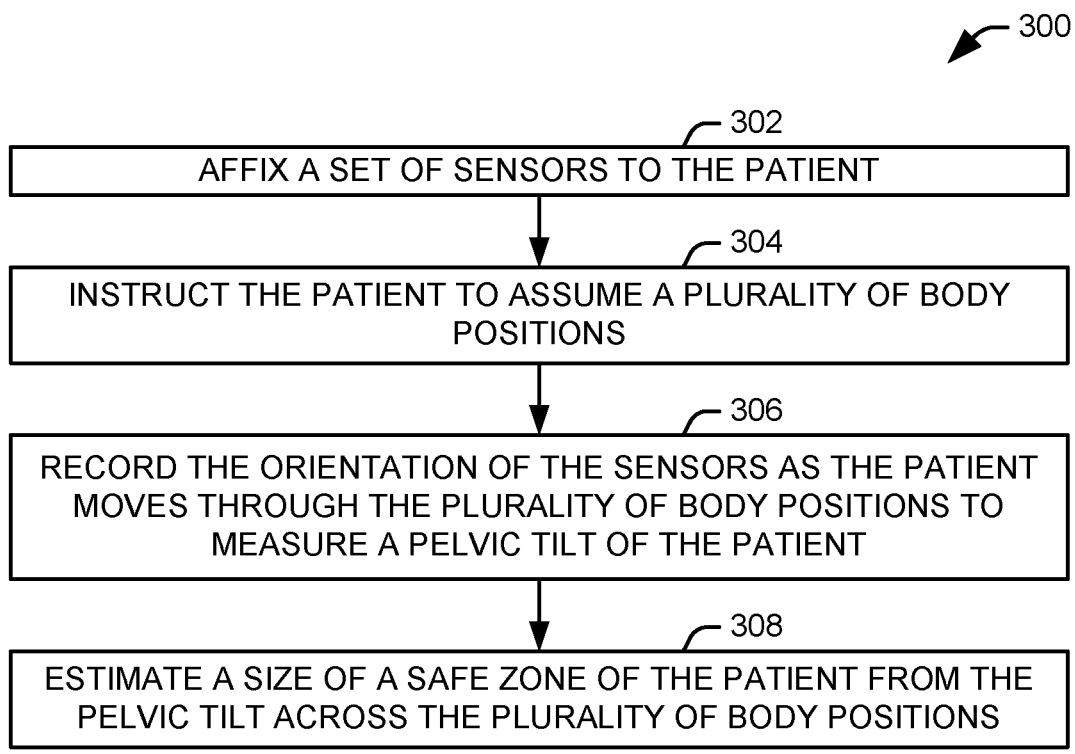
FIG. 3 illustrates one example of a method for providing an initial classification for a size of a safe zone of a patient.
Figure 4:
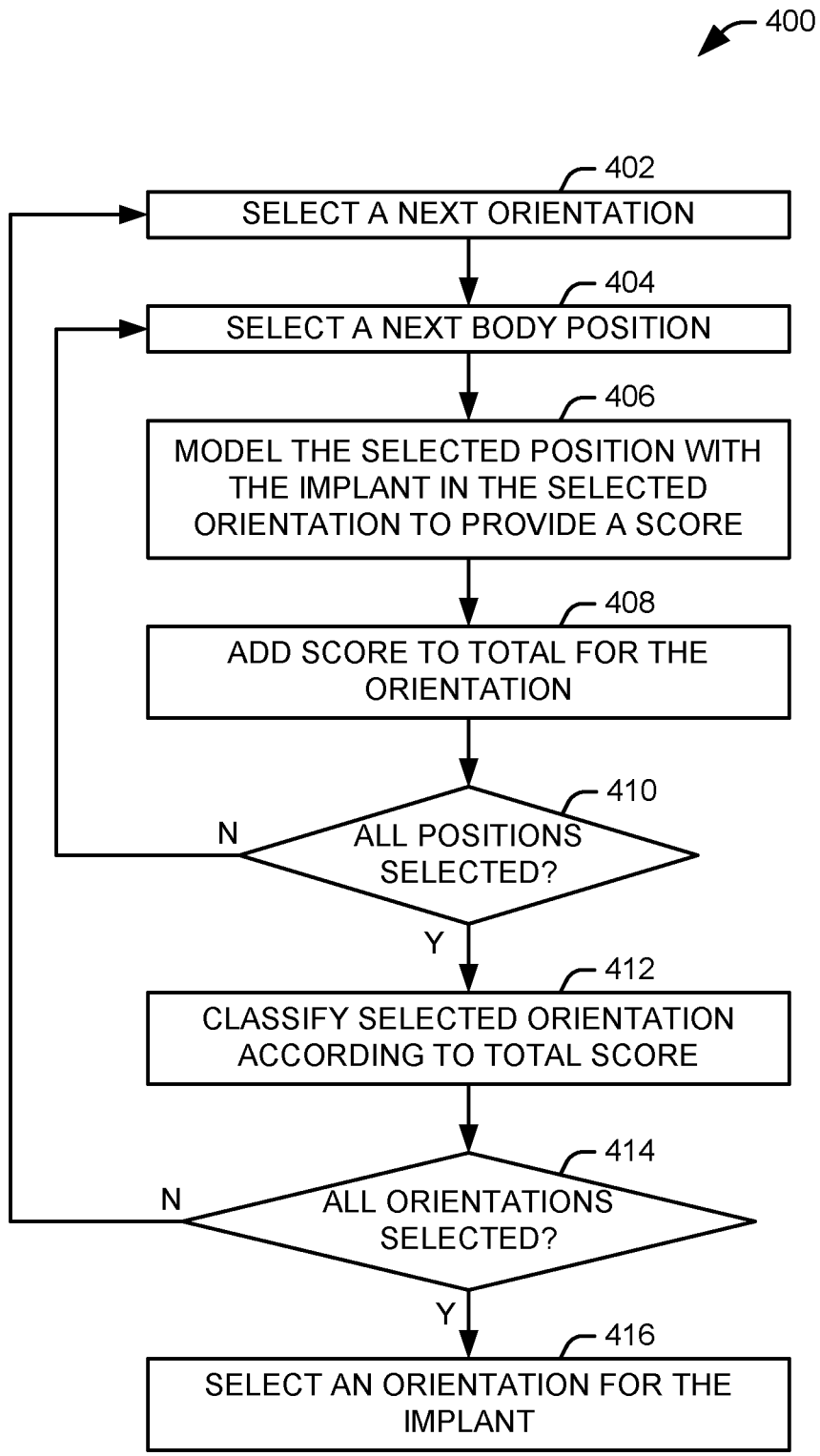
FIG. 4 illustrates one example of a method for selecting an orientation for an implant according to simulated relative motion.

In view of the foregoing structural and functional features described above, methods in accordance with various aspects of the present invention will be better appreciated with reference to FIGS. 2-4. While, for purposes of simplicity of explanation, the methods of FIGS. 2-4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 2 illustrates a method 200 for surgical planning. At 202, an initial classification of a patient is determined according to a safe zone determined from a pelvic tilt in a plurality of body positions. The pelvic tilt is measured as a position of a pelvis of the patient relative to the position of a spine of the patient. In one implementation, the change in the pelvic tilt of the patient as the patient moves through a series of positions can be measured using a set of accelerometers attached to the body and an application on a mobile device. The measured change in the pelvic tilt between positions can be used to classify the patient into a various classes representing the size of the "safe zone" for positioning and orienting the implant.

At 204, a model of a pelvis of the patient is constructed according to the initial classification of the patient. In one implementation, patients in a first class, representing a large safe zone, can be evaluated with a default model that is adjusted to account for external measurements of the patient. Patients in a second class, representing a moderately sized safe zone, can be evaluated using a model that is generated by capturing a plurality of x-ray images of the patient and warping an atlas model of the pelvis to register it to the captured images. Patients in a third class, representing a small safe zone, can be evaluated using a model that is generated via a computed tomography (CT) scan. As a result, exposure to ionizing radiation can be significantly reduced or even eliminated for patients determined to have a large safe zone.

At 206, relative motion of the model of the pelvis and a model of an implant is simulated, for example, via a finite element modeling system. At 208, at least one of a position of the implant and an orientation of the implant for the patient is selected according to the simulated relative motion. In one implementation, the implant can be placed at a desired orientation, defined by version and inclination, within the model, and the model can be moved through a series of motions. During the motions, potential problems with the implant, such as edge loading and impingement, can be detected and used to calculate a desirability score for each orientation. The orientation can be selected, for example, as an orientation with the best score or as the centroid of a region of orientations having a threshold desirability score.

FIG. 3 illustrates one example of a method 300 for providing an initial classification for a size of a safe zone of a patient. At 302, a set of sensors is affixed to the patient. For example, the set of sensors can be a set of tri-axis accelerometers positioned to measure a pelvic tilt of the patient. At 304, the patient is instructed to assume a plurality of body positions. For example, the body positions can include commonly assumed positions (e.g., sitting, standing, supine) as well as positions associated with implant dislocation or other complications. At 306, the orientation of the sensors as the patient moves through the plurality of body positions is recorded to measure a pelvic tilt of the patient.

At 308, a size of a safe zone of the patient is estimated from the pelvic tilt across the plurality of body positions. In one implementation, the size of the safe zone is determined from a linear combination of the measured pelvic tilts, for example, via a look-up table populated from previous patient data. In another implementation, a multidimensional mapping is assigned to the patient for each of the plurality of body positions, representing an average safe zone for patient having a similar pelvic tilt in that body position across at least two parameters representing the orientation and position. For example, the parameters can represent the inclination and version of an implant being considered for the procedure. The multidimensional mappings are then across the plurality of body positions to estimate a safe zone for the patient.

FIG. 4 illustrates one example of a method 400 for selecting an orientation for an implant according to simulated relative motion. At 402, a next orientation is selected. In the illustrated implementation, each orientation is an ordered pair of inclination and version, representing a two-dimensional array of values at a desired resolution within a range of feasible values for the inclination and version. In a first iteration, a default orientation and inclination can be selected. At 404, a next motion of a series of motions is selected. The series of motions can represent common motions that a patient might be expected to perform as well as motions known to be likely to cause a dislocation or other problem with the implant.

At 406, the selected motion is modelled with the implant in the selected orientation to provide a desirability score. A finite element model of the pelvis and the implant can be employed to evaluate the selected motion, with the risk of excessive wear and dislocation evaluated according to component interrelation and the relation of components to neighboring bones and tissue structures. At 408, the score is added to the score for the orientation. At 410, it is determined if all motions have been evaluated. If not (N), the method returns to 404 to select a next motion for evaluation.

Once all motions have been evaluated, the selected orientation is classified into one of a plurality of classes at 412 according to the sum of the desirability scores. In one implementation, the plurality of classes can include an "unacceptable" class, an "acceptable" class, and a "preferred" class, representing a best overall desirability class. In an alternative implementation, the classes can be more discrete, each representing a smaller range of desirability values, such that a two-dimensional heat map can be formed to display the suitability of each inclination and version pair. Once a class has been selected, the method advances to 414, where it is determined if each orientation has been selected. If not (N), the method returns to 402 to select a next orientation.

Once all orientations have been selected (Y), the method advances to 416, where an orientation for the implant can be selected. In one implementation, an orientation with a best desirability score can be selected. Alternatively, a region representing orientations with a threshold level of desirability, that is, in the preferred class, can be defined, and an orientation representing a centroid of that region can be selected. The classifications can also be displayed to a surgeon as a two-dimensional mapping, allowing the surgeon to make the final selection. Once the orientation is selected, the method terminates.

Figure 5:
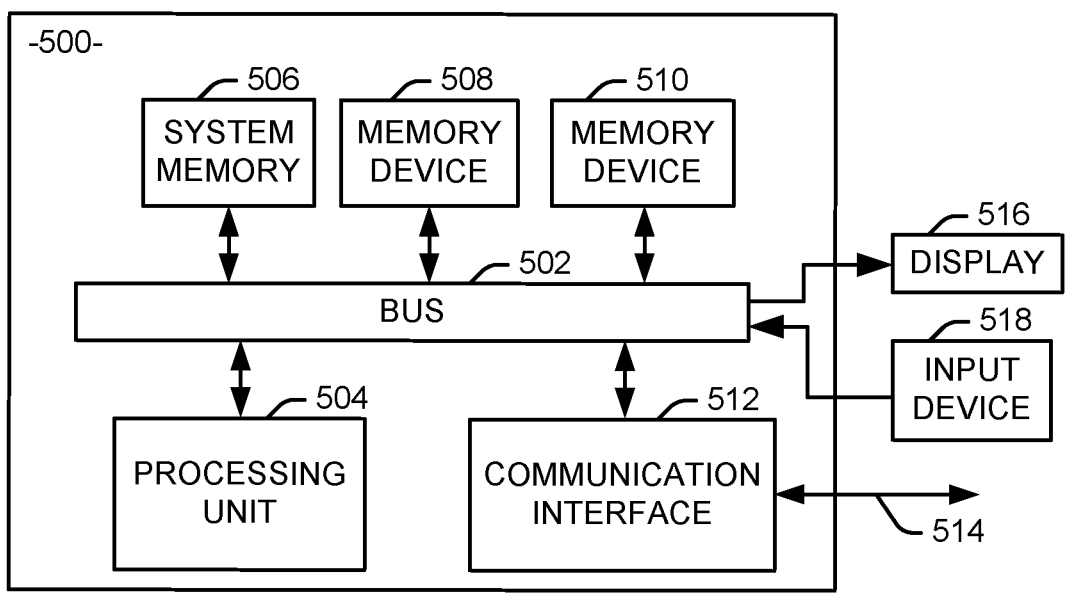
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 500 of hardware components capable of implementing examples of the systems and methods disclosed in FIGS. 1-4. The system 500 can include various systems and subsystems. The system 500 can be a personal computer, a laptop computer, a workstation, a computer system, an appliance, an application-specific integrated circuit (ASIC), a server, a server blade center, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard and/or a mouse). The system bus 502 can be in communication with the processing unit 504 and the system memory 506. The additional memory devices 508 and 510, such as a hard disk drive, server, stand alone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508 and 510 can store data, programs, instructions, database queries in text or compiled form, and any other information that can be needed to operate a computer. The memories 506, 508 and 510 can be implemented as computer-readable media (integrated or removable) such as a memory card, disk drive, compact disk (CD), or server accessible over a network. In certain examples, the memories 506, 508 and 510 can comprise text, images, video, and/or audio, portions of which can be available in formats comprehensible to human beings.

Additionally or alternatively, the system 500 can access an external data source or query source through the communication interface 512, which can communicate with the system bus 502 and the communication link 514.

In operation, the system 500 can be used to implement one or more parts of a surgical planning system in accordance with the present invention. Computer executable logic for implementing the surgical planning system resides on one or more of the system memory 506, and the memory devices 508, 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skills in the art will recognize that many further combinations and permutations of the present invention are possible. Accordingly, the present invention is intended to embrace all such alterations, modifications, and variations that fall within the scope of the appended claims.

Having described the invention, we claim:

1. A method comprising:
   providing an initial classification of a patient according to a safe zone determined from a pelvic tilt, measured as a position of a pelvis of the patient relative to the position of a spine of the patient, in a plurality of body positions;
   constructing a model of a pelvis of the patient according to the initial classification of the patient;
   simulating relative motion of the model of the pelvis and a model of an implant via a finite element modeling system; and
   selecting at least one of a position of the implant and an orientation of the implant for the patient according to the simulated relative motion;
   wherein simulating relative motion of the model of the pelvis and an model of an implant comprises repeating a series of motions for each of a number of orientations of the implant and selecting the at least one of the position of the implant and the orientation of the implant for the patient according to the simulated relative motion comprises generating a two-dimensional map for each motion of the series of motions, each of a plurality of points on the two-dimensional map representing a desirability score for an ordered pair representing an inclination and version of the implant.

2. The method of claim 1, wherein the desirability score comprises an edge loading score that represents a contact area between various portions of the implant during the series of motions.

3. The method of claim 1, wherein the desirability score comprises an impingement score that represents a degree of implant-on-implant impingement, implant-on-bone impingement, and bone-on-bone impingement during the series of motions.

4. The method of claim 3, wherein the desirability score is a linear combination of the impingement score and an edge loading score that represents a contact area between various portions of the implant during the series of motions.

5. The method of claim 1, wherein selecting the at least one of the position of the implant and the orientation of the implant for the patient according to the simulated relative motion comprises generating a linear combination of the desirability score for each point across the two-dimensional maps for the series of motions.

6. The method of claim 5, wherein the linear combination is a weighted linear combination wherein the weights for the weighted linear combination are determined according to a frequency with which the patient is expected to perform each motion of the series of motions.

7. A method comprising:
   providing an initial classification of a patient according to a safe zone determined from a pelvic tilt, measured as a position of a pelvis of the patient relative to the position of a spine of the patient, in a plurality of body positions, wherein providing an initial classification of a patient according to a safe zone determined from a pelvic tilt comprises:
   measuring a pelvic tilt at each of the plurality of body positions;
   assigning a multidimensional mapping to the patient for each of the plurality of body positions, representing an average safe zone for patient having a similar pelvic tilt in that body position across at least two parameters representing the orientation and position; and
   combining the multidimensional mappings across the plurality of body positions to estimate a safe zone for the patient;
   constructing a model of a pelvis of the patient according to the initial classification of the patient;
   simulating relative motion of the model of the pelvis and a model of an implant; and
   selecting at least one of a position of the implant and an orientation of the implant for the patient according to the simulated relative motion
   wherein simulating relative motion of the model of the pelvis and the model of an implant comprises repeating a series of motions for each of a number of orientations of the implant and selecting the at least one of the position of the implant and the orientation of the implant for the patient according to the simulated relative motion comprises generating a two-dimensional map for each motion of the series of motions, each of a plurality of points on the two-dimensional map representing a desirability score for an ordered pair representing an inclination and version of the implant.

8. The method of claim 7, wherein the multidimensional mapping is a two-dimensional mapping, and the at least two parameters are an inclination and version of the implant.

9. The method of claim 7, wherein combining the multidimensional mappings across the plurality of body positions to estimate a safe zone for the patient comprises averaging corresponding values of the multidimensional mappings across the plurality of body positions.

10. The method of claim 7, wherein combining the multidimensional mappings across the plurality of body positions to estimate a safe zone for the patient comprises generating a final map having a safe zone including only values that met a threshold value within each multidimensional mapping for the plurality of body positions.

* * * * *